United States Patent
Thiran et al.

(10) Patent No.: US 8,617,180 B2
(45) Date of Patent: Dec. 31, 2013

(54) ADJUSTABLE STEREOTACTIC DEVICE AND METHOD FOR FRAMELESS NEUROSURGICAL STEREOTAXY

(75) Inventors: Jean-Philippe Thiran, St-Légier (CH); Claudio Pollo, Lausanne (CH)

(73) Assignees: Ecole Polytechnique Fédérale de Lausanne (EPFL), Lausanne (Ecublens) (CH); Université de Lausanne, Lausanne (CH)

( * ) Notice: Subject to any disclaimer, the term of this patent is extended or adjusted under 35 U.S.C. 154(b) by 290 days.

(21) Appl. No.: 12/741,533

(22) PCT Filed: Nov. 5, 2008

(86) PCT No.: PCT/IB2008/054617
§ 371 (c)(1),
(2), (4) Date: Oct. 18, 2010

(87) PCT Pub. No.: WO2009/060394
PCT Pub. Date: May 14, 2009

(65) Prior Publication Data
US 2011/0190789 A1     Aug. 4, 2011

(30) Foreign Application Priority Data
Nov. 5, 2007   (WO) ................ PCT/EP2007/061901

(51) Int. Cl.
*A61B 19/00*       (2006.01)
(52) U.S. Cl.
USPC ........................... 606/130; 600/424; 600/429
(58) Field of Classification Search
USPC ........................... 606/130; 600/417, 429, 424
See application file for complete search history.

(56) References Cited

U.S. PATENT DOCUMENTS 6,529,765 B1 *  3/2003  Franck et al. ................ 600/427
2007/0106305 A1  5/2007  Kao et al.

FOREIGN PATENT DOCUMENTS

| WO | WO 95/13758 | 5/1995 |
| WO | WO 2007/031314 | 3/2007 |
| WO | WO 2007/095917 | 8/2007 |

OTHER PUBLICATIONS

International Search Report for PCT/IB2008/054617, mailed Apr. 14, 2009.
Written Opinion of the International Searching Authority for PCT/IB2008/054617, mailed Apr. 14, 2009.

* cited by examiner

*Primary Examiner* — Katherine Dowe
*Assistant Examiner* — Katrina Stransky
(74) *Attorney, Agent, or Firm* — Nixon & Vanderhye P.C.

(57) ABSTRACT

The system comprises at least three anchors (2,2',2") intended to be attached to the patient and equipped with markers (5,5',5"), an insertion guide device (6) with an insertion guide (7) intended to be attached to said anchors (2,2', 2"), an external calibration device (8) with at least three calibration markers (10,10',10") corresponding to said markers (5,5',5") and a planning and imaging software. The planning and imaging software is used to determine the position of a target point in the patient with respect to the markers (5,5', 5"), the calibration device is used to calibrate and orient the insertion guide (7) of the insertion guide device (6) mounted on said calibration markers (10,10',10") using the determination of the software before the insertion guide device is mounted on said markers (5,5',5") attached to the patient.

11 Claims, 4 Drawing Sheets

ADJUSTABLE STEREOTACTIC DEVICE AND METHOD FOR FRAMELESS NEUROSURGICAL STEREOTAXY

This application is the U.S. national phase of International Application No. PCT/IB2008/054617 filed 5 Nov. 2008, which designated the U.S. and claims priority to EP Application No. PCT/EP2007/061901 filed 5 Nov. 2007, the entire contents of each of which are hereby incorporated by reference.

FIELD OF INVENTION

The present invention relates to stereotactic surgery and more precisely to frameless neurosurgical stereotaxy.

STATE-OF-THE-ART

Stereotactic surgery, also called stereotaxy, is a minimally-invasive form of surgical intervention which makes use of a three-dimensional coordinates system to locate targets inside the body and to perform on them some action such as ablation (removal), biopsy, lesion (thermo-lesion, X-Ray or Gamma-ray induced lesion), injection, electrical stimulation, implantation, etc. "Stereotactic" in Greek (another accepted spelling is "stereotaxic") means movement in space.

In neurosurgery, stereotactic procedures refer to the use of a reference frame, a mechanical device equipped with head-holding clamps and bars which puts the head in a fixed position in reference to the coordinate system (the so-called zero or origin) of the frame. Each point in the brain can then be referenced by its three coordinates (x, y and z) in an orthogonal frame of reference (Cartesian coordinates), or, alternatively, a polar coordinates system, also with three coordinates: angle, depth and antero-posterior location. The standard way of defining target points in stereotactic neurosurgical procedures consists in imaging the patient's head in three dimensions (3D) by Computed Tomography (CT) or Magnetic Resonance Imaging (MRI) while holding the stereotactic frame (or a subset of it). Since both the brain and the frame are visible on the images, the coordinates of the target point can be defined in the coordinate system of the frame, either directly on images when the target is clearly identifiable or with the help of stereotactic atlases. Finally, guide bars in the x, y and z directions (or alternatively, in the polar coordinate holder), fitted with high precision scales, allow the neurosurgeon to reach the target with a probe (electrode, needle, cannula, X-ray or Gamma-ray beam, etc.) inside the brain, at the calculated coordinates for the desired structure, following an optimal trajectory through a small twist drill in the skull.

The main advantage of this procedure is its high precision.

Moreover, stereotaxy is a classical procedure in neurosurgical practice: every neurosurgeon is trained for this procedure.

Its main drawbacks are clear though:
the feeling of pressure and pain during and after the placement of the frame, which has to be held by the patient for several hours, all along the imaging and surgical procedures,
the immobilization of the head at the OR table during the surgical procedure, that may result in a discomfort due to the duration of some operations (several hours) and in a highly unsuitable displacement of the frame on the patient's head if he/she tried to move during the operation, leading to a severe loss of precision in the probe placement,
potential artifacts in MR imaging performed with stereotactic frame, due to the distortion of the magnetic field of the MR scanner, induced by the frame, that may lead to loss of precision in targeting on such images.

Therefore researchers have tried to propose alternatives to stereotactic frames, while keeping the high precision as a strict requirement.

The main efforts have been made in the combination of imaging and neurosurgical robots: small fiducial markers are placed on the skull of the patient. The 3D imaging (either CT or MRI) is done, and adequate calibration/registration procedure is then used to register the coordinate system of a robot arm with the coordinate system of the patient head, defined by the fiducial markers. Then the robot arm can be placed in a pre-defined position and orientation defined with respect to the patient head, and either serve as a guide/support for inserting the surgical tools (needle, electrode, etc) or doing the insertion itself (drilling, etc) under the control of the neurosurgeon. While it partially fulfills the precision requirements and minimizes the patient discomfort, the main drawbacks of such systems are the high level of complexity in using, calibrating and maintaining them, and most importantly their prohibitive cost, which makes such system only affordable for a very limited number of hospitals in the world. Finally, there is an intrinsic procedural danger in having a robot moving independently of the head. For all those reasons, neurosurgical robot systems are not competitive as compared to classical stereotactic frames.

At the beginning of the years 2000, the Vanderbilt University Medical Centre, Nashville, Tenn., introduced the STarFix technology which consists in a patient-specific tripod, specially realized for each patient. The procedure is as follows: based on the intended entry area location, anchors, similar to fiducial markers, are screwed on the patient's head, and the patient is then scanned by CT or MRI. Then surgical planning software is used to define the target point with respect to the coordinate system defined by the anchors. Then the corresponding data are sent (by Internet) to the manufacturer (FHC Inc. Bowdoinham, Md., USA) which realizes a personalized tripod, called the STarFix. This tripod is then fixed on the patients head using the anchors. Guiding tools are fixed to the tripod to realize the operation. More details can be found on the internet at http://www.fh-co.com/p67-69B.pdf The advantages of this procedure are its low complexity and increased comfort of the patient, as well as its compatibility with several guidance and tool holding devices. Other advantages include the precision (similar to the frame-based procedure), simplicity and efficiency.

But there are several important drawbacks:

A new tripod has to be realized by the manufacturer for each surgical operation. The realization takes between 1 and 3 days. Moreover the company is located in the USA, which may induce additional delays in shipping the tripod from the manufacturer to the user when the patient undergoes surgery in another country or continent.

Accordingly, during this period, the anchors have to stay implanted on the patient head, which may cause pain and potential infections.

Most importantly, once the tripod is realized, there is no way to modify the surgical planning: the tripod being strictly based on the pre-operative planning, the trajectory can absolutely not be changed during the operation, to adapt to unexpected events.

Any change in the planning would require the realization of a new tripod, i.e. another 1 to 3 day delay with the drawbacks mentioned above if the patient is not in the USA.

Typical examples of stereotaxy devices are described in the following publications: WO 2004/058086, U.S. 2006/0192319, U.S. Pat. No. 6,282,437 and WO 2005/039386.

GENERAL DESCRIPTION OF THE INVENTION

The present invention introduces a new way of setting the geometry of an insertion guide device, fixed on the patient's head, using an external calibration device, resulting in a miniaturization of the elements fixed on the patient's head while keeping the advantages of the stereotactic procedure, in terms of precision and simplicity.

In one aspect, the invention is made of three principal components: an insertion guide device, a calibration device and image-based surgical planning software.

A caliber is used to guide the implantation of three anchors on the patients head. It is made for example of a ring with three spherical joints holding the three anchors such that the centers of these three joints are in a fixed geometry.

The three anchors, are fixed on patient skull (for example implanted in the patient's skull or attached by other equivalent means) using the caliber. They are designed to fix locators and the tripod itself on the patient's head as will be described hereunder.

The tripod is basically made of a central spherical joint, bored with a hole that will serve as a guide for the insertion of the surgical tools (needle, electrode, etc.). This central joint is supported by three legs, in a fixed geometry. At the end of each leg, a spherical joint holds a fixation system that will be attached on the anchors of the patient. The centers of those three spherical joints are exactly in the same geometry as the centers of the joints of the caliber, i.e. they form exactly the same triangle. Additionally, the central joint of the tripod is mounted on a moving table, (so-called x-y table) that allows very precise and controlled displacement of the joint in the plan of the tripod head, using two micrometric screws.

The calibration device is used to set the orientation of the central spherical joint of the tripod to reach the target point, based on the surgical planning.

The surgical planning software allows simulating and planning the whole operation, and returns values used to fix the central spherical joint of the tripod in the required orientation, using the calibration device.

DETAILED DESCRIPTION OF THE INVENTION

The invention will be better understood below with a detailed description of a typical stereotactic intervention on the head of a patient using a system according to the present invention and with reference to the exemplary figures.

Figure 1:
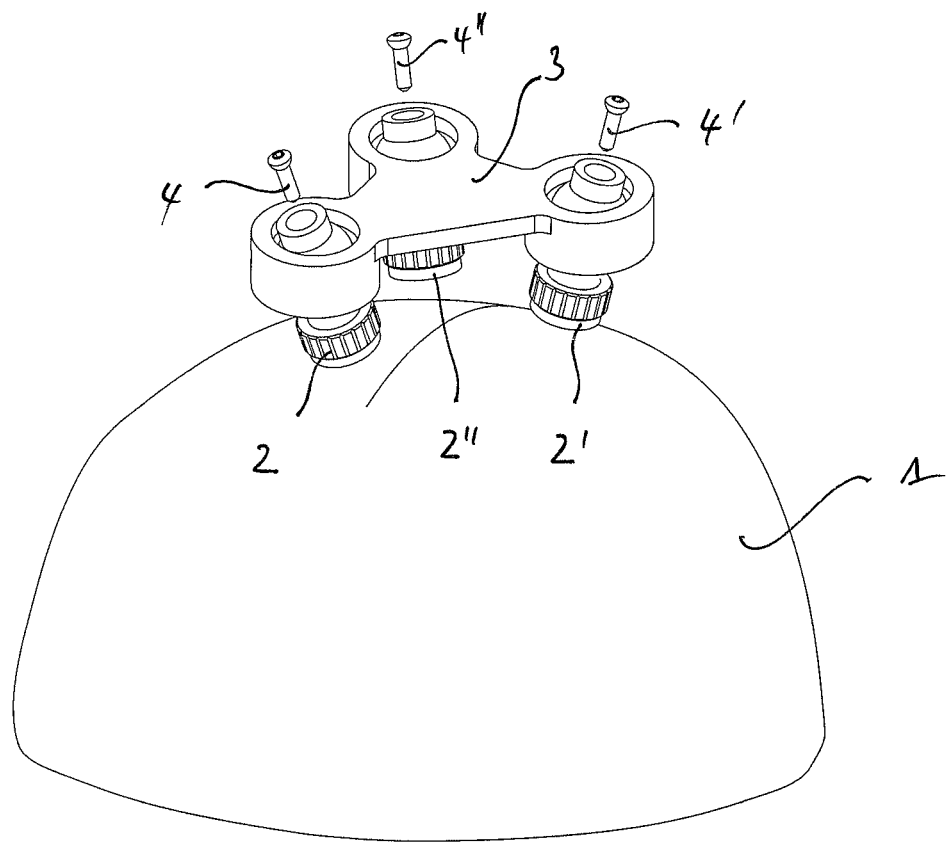
FIG. 1 illustrates the "calibre" allowing the placing of three anchors in an appropriate geometry.
Figure 2:
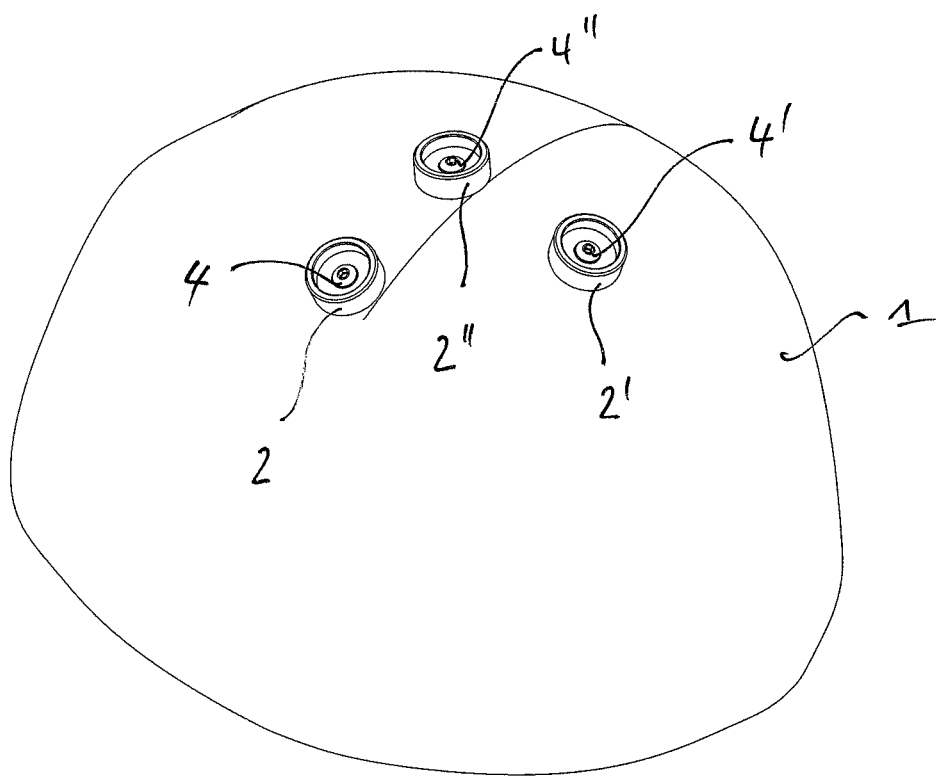
FIG. 2 illustrate the three anchors placed on the skull of a patient.
Figure 3:
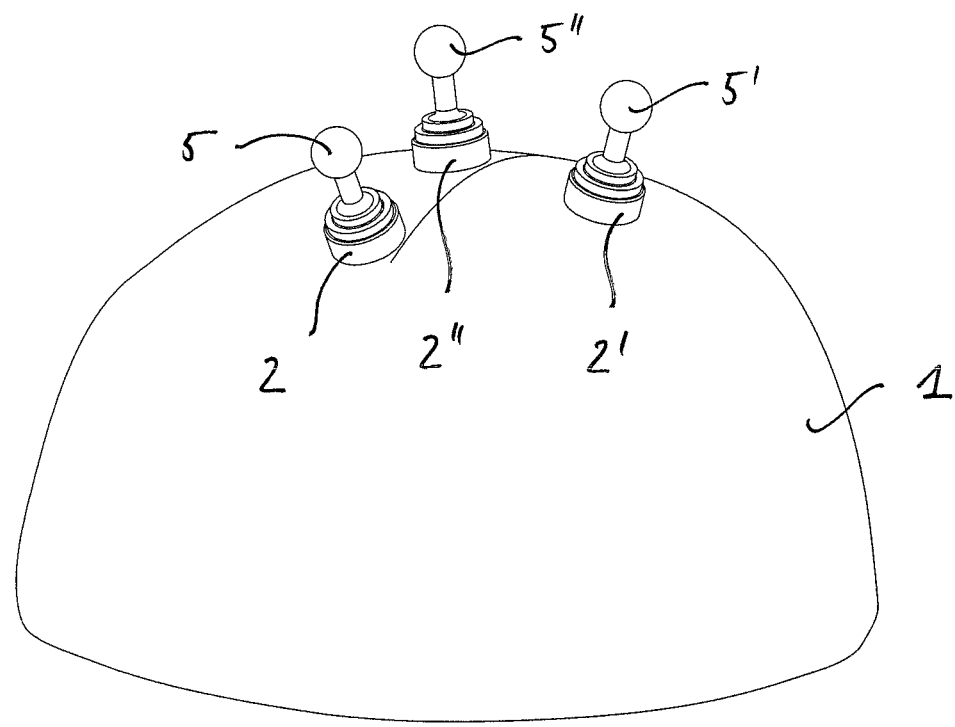
FIG. 3 illustrates locators (markers) fixed on the anchors.

As illustrated in FIG. 1, considering a target point 12 in the brain and an entry point in the skull 1, as imagined by the neurosurgeon before a surgical operation (based on pre-operative imaging for example or any other investigation mean), the surgeon implants at least three anchors 2, 2', 2" in the patient's head, positioned such a way that markers 5, 5', 5" (see FIG. 3) that will be fixed on those anchors will be in a precise pre-defined relative position (pre-defined geometry) for example through a calibre 3. In the case of three anchors 2, 2', 2" as illustrated, this means that the markers 5, 5', 5", more specifically the centre of the round ends of the markers, have to form a precise pre-defined triangle corresponding the to the calibration device as explained later hereunder. To do this, the surgeon can for instance use the calibre 3, i.e. a rigid device allowing positioning the three anchors 2, 2', 2" according to the desired relative position. This situation is illustrated in FIG. 2 where the three anchors 2, 2', 2" are attached to the skull 1 for example each by a screw 4, 4', 4" or other equivalent means in such a position that the markers that will be attached to them will be in the predetermined relative position. Of course, one may use more than three anchors if desired.

A locator or marker 5, 5', 5" is then attached (for instance screwed or fixed by any other suitable equivalent means) on each of said anchor 2, 2', 2". These markers 5, 5', 5" are made with material compatible with the imaging system used (e.g. CT or MRI) and visible on the images produced by the imaging system used. Then the patient is scanned, to produce a 3D image volume of his/her head, where the markers 5, 5', 5" and the target of the surgery are clearly visible and can be identified.

The 3D images of the patient with the markers are then loaded in a surgical planning software. The images are displayed on a screen of a computer, for instance in an orthogonal mode, i.e. displaying three orthogonal sections of the volume at the same time. Other or complementary display modes are also possible, such as 3D rendering. Then the locations of the target point 12 and of the three makers 5, 5', 5" are identified on the displayed images. This can be done manually, the user identifying those points with a mouse or other equivalent means. Alternatively or complementarily, automatic image analysis algorithms can be used to perform this task. Additionally, the target point 12 of the surgery has to be identified, manually or by any automatic means, on the same image volume. This allows calculating the relative position of the target point 12 with respect to the referential made of the markers 5, 5', 5".

At a later stage in order to carry out the surgical procedure, an insertion guide device 6 will be fixed on the anchors 2, 2', 2" of the patient, and a surgical instrument 14 (electrode, needle, cannula) will be inserted in the brain, through a small hole 15 drilled in the skull 1, through an insertion guide 7 of the insertion guide device 6. The insertion guide device 6 is made of a mobile part holding the insertion guide 7, which can be freely rotated to be pointed to the target point 12. The key issue is to precisely orient this mobile part towards the target point 12.

Figure 4:
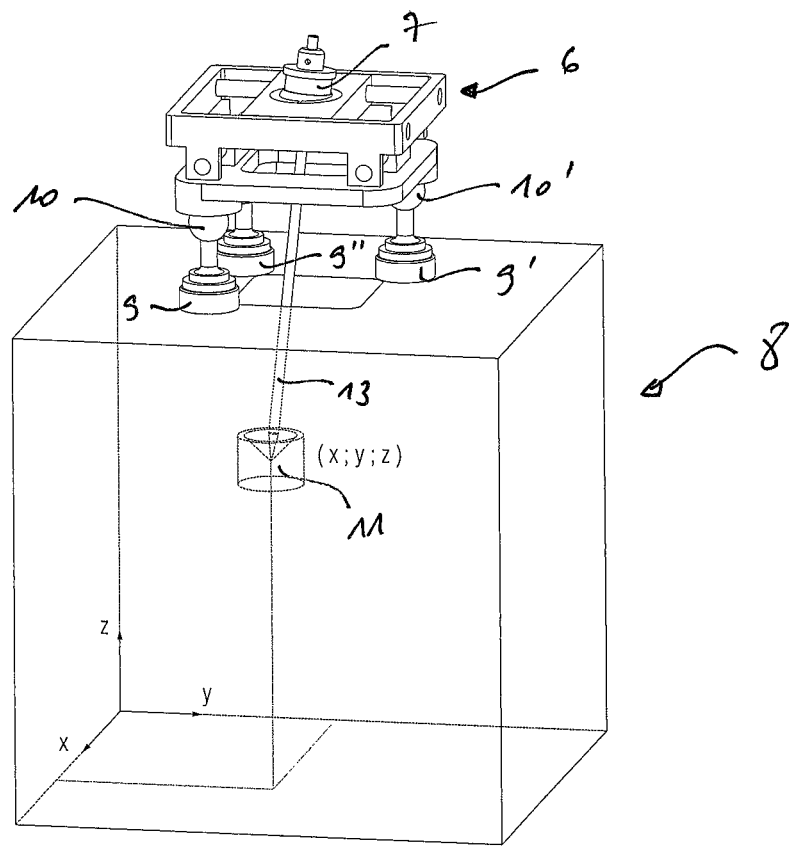
FIG. 4 illustrates a calibration device with the insertion guide device on it, with the calibration target point at position (x, y, z) defined by the surgical planning software.

In order to achieve this goal, according to the present invention, a calibration device 8 is used (see FIG. 4). This calibration device 8 carries a group of calibration anchors 9, 9', 9", their number being identical to the number of the anchors 2, 2', 2' carried by the patient. Each calibration anchor 9, 9', 9" carries a calibration marker 10, 10', 10" identical to the markers 5, 5', 5" and the relative position of their round ends being the same as of that of the markers 5, 5', 5" previously fixed on the patient's skull. Preferably, according to the invention, the position of the calibration anchors 9, 9', 9" is fixed such that the calibration markers 10, 10', 1'0' are also fixed with a given relative position of the centre of their round end and the calibre 3 is used to maintain the anchors in a corresponding position such that the markers 5, 5', 5" have the same relative position of their round ends.

As can be understood, this calibration device 8 allows placing a calibration target point 11 at the same position, relatively to the calibration anchors 9, 9', 9" and calibration markers 10, 10', 10" of the calibration device, as the position of the real target 12, relatively to the markers 5, 5', 5" fixed on the patient's skull. Placement of the calibration target point 10 can for instance be realised by a micrometric x-y-z table or by other equivalent means. As described above, the relative position of the real target 12 with respect to the markers 5, 5', 5" is preferably defined in the surgical planning phase by the surgical planning software. Of course, other equivalent methods may be used to achieve this goal.

Then the insertion guide device 6 is placed on the calibration markers 10, 10', 10" of the calibration device 8, on the side opposite to the calibration target point 11. A surgical calibration device 13 such as a needle, similar or identical to the surgical device 14 that will be used during the surgery, is inserted in the insertion guide 7, which is kept free to rotate. The calibration surgical device 12 is then manually or automatically moved and adjusted to precisely touch the calibration target point 11. Once in place, the insertion guide device 6 is tightly blocked, such that the orientation and position of the guide 7 can not change anymore.

The insertion guide device 6 is then removed from the calibration markers 10, 10', 10" of the calibration device 8 and transferred on the markers 5, 5', 5" attached to the patient. The markers 5, 5', 5" can be the one used for the imaging step mentioned above, or, alternatively, they can be replacement markers 16, 16', 16" (not shown) that are made in another material. See, e.g., FIG. 5. Indeed, such markers that are visible on images of human patients can be quite expensive to produce, and it can thus be interesting to replace the markers used for imaging by other markers made of a cheaper material. Another advantage in such a process is to use replacement makers that are sterile which may not be the case of the markers used for imaging, once the imaging step has been completed.

Figure 5:
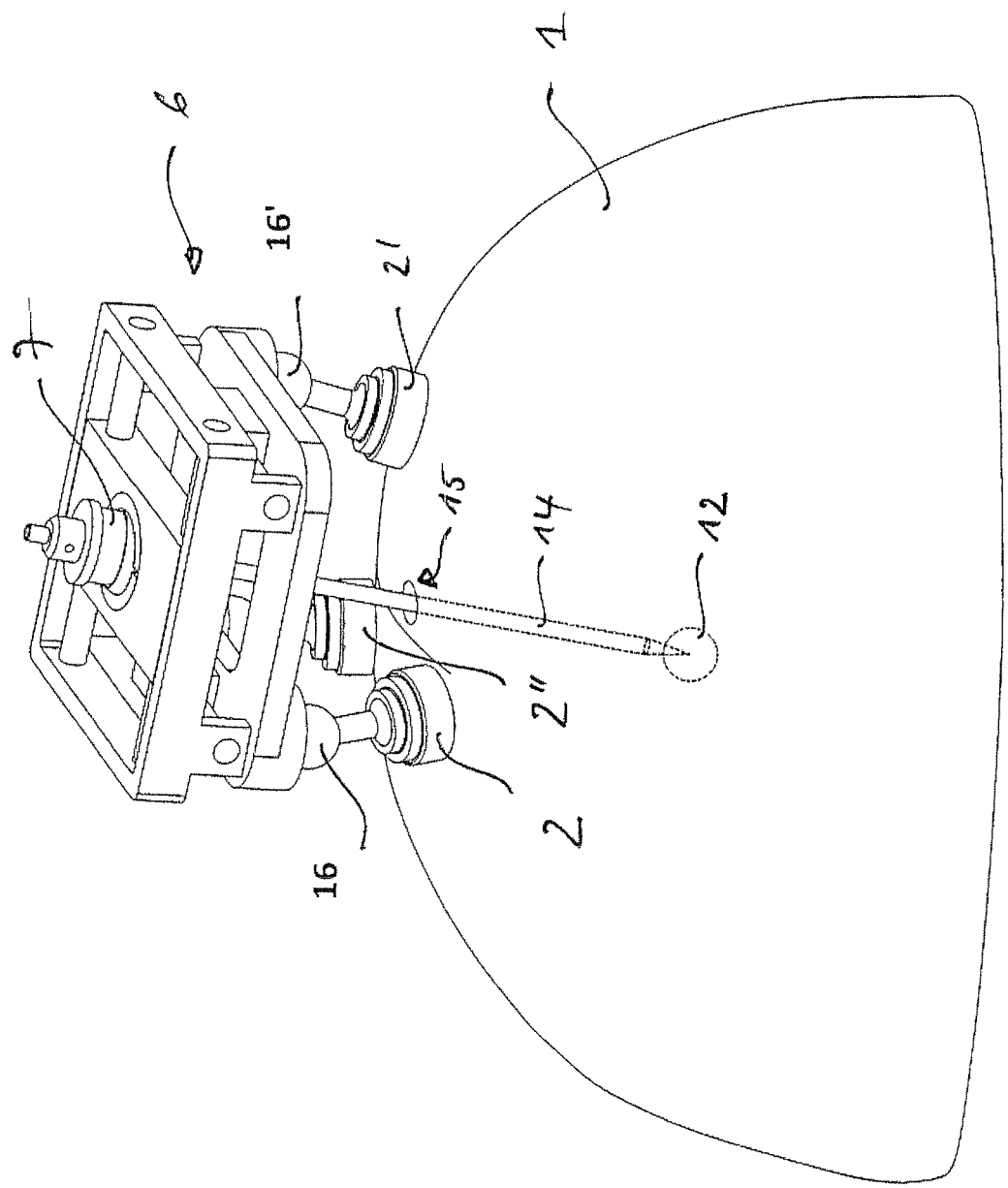
FIG. 5 illustrates the insertion guide device placed on the anchors on the head of the patient.
Figure 6:
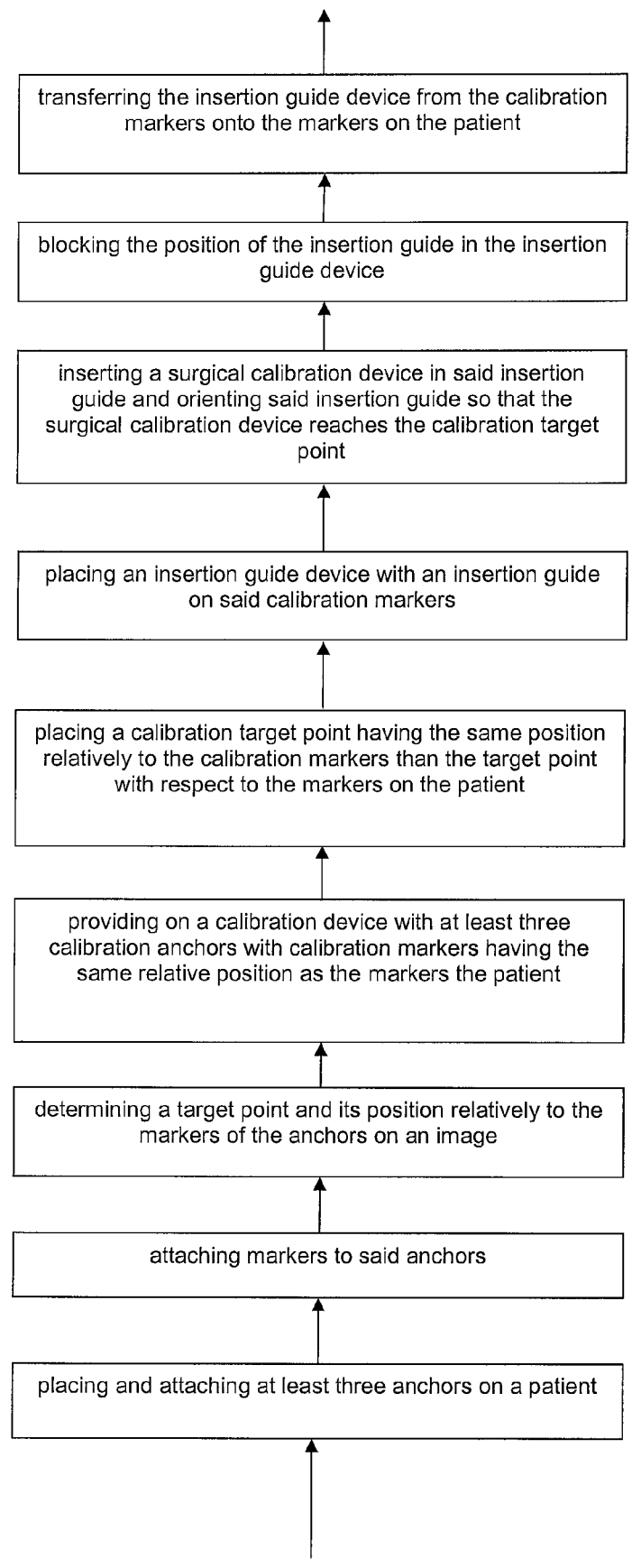
FIG. 6 illustrates a block diagram of a method according to the invention

By this mean, the insertion guide 7 is guaranteed to be oriented precisely towards the real target point 12 of the surgery that has been reproduced in the calibration step of the device. The surgeon can now remove the surgical calibration device 13 and insert the surgical device 14 (if different from the surgical calibration device 13) in the head of the patient through a hole 15. This is illustrated in FIG. 5.

Additionally, the insertion guide device 6 can be equipped with a mobile part, allowing to shift the axis of the insertion guide 7 very precisely in the plane of the insertion guide device 6. A small micrometric x-y table can be used for this purpose or other equivalent means. This can be used to slightly shift the planned trajectory during the operation to reach nearby target points, or to change the entry point of the instrument in the skull, for instance to avoid a vein or any other obstacle on the trajectory. The definition of the shift (x and y displacements) can be defined based on the images displayed in the special surgical planning software, and reported on the insertion guide device 6 prior to the calibration step. It can also be changed during the operation of the surgeon decides to do so.

A method according to the present invention comprises at least the following steps:
  placing and attaching at least three anchors on a patient
  attaching markers to said anchors, said markers having a predetermined relative position;
  acquiring one or several 3D images of the patient's head, where the target point of the surgery and the markers are visible;
  determining a target point and its position relatively to the markers of the anchors on said images;
  providing a calibration device with at least three calibration markers having the same relative position as the markers on the patient;
  placing a calibration target point having the same position relatively to the calibration markers than the target point with respect to the markers on the patient;
  placing an insertion guide device with an insertion guide on said calibration supports;
  inserting a surgical calibration device in said insertion guide and orienting said insertion guide so that the surgical calibration device reaches the calibration target point;
  blocking the position of the insertion guide in the insertion guide device;
  transferring the insertion guide device from the calibration markers onto the markers on the patient in order to be able to carry out a surgical intervention.

As has been indicated above, preferably one uses at least three markers on the patient, but a higher number may be envisaged as well. Also, the marker can be attached later to the anchors, or they can be integrated into the anchors.

As mentioned, the markers on the patient can be the same throughout the entire process, or one can use a first set of markers for the imaging step (i.e. markers that are properly visible on the produced images) and another set of markers for the surgical intervention, said other set of markers be made of a cheaper material. Accordingly, one preferably uses markers that can be attached and removed from the anchors.

The markers and the target point can be determined on an image automatically or manually by a user (for example a surgeon). Also, other equivalent techniques may be used instead of imaging.

Preferably, the relative position of the calibration markers 10, 10', 10" on the calibration device 8 are fixed and this relative position is reproduced with the markers 5, 5', 5" attached to the patient. This is done for example through the calibre 3 used to place the anchors 2, 2', 2". Of course other equivalent means than the calibre may be used to achieve this goal.

Also one may envisage to attach the anchors 2, 2', 2" and the markers 5, 5', 5" to the patient, then to measure the relative position of the markers 5, 5', 5" and to reproduce this same relative position on the calibration anchors 10, 10', 10".

As compared to the existing techniques, the present invention overcomes all the drawbacks of the STarFix system:
  the device is not designed for one given patient, but can be adapted to any patient, and thus re-used from one patient to the other. It is therefore always available. The delay introduced by the realization of a customized tripod by a manufacturer like FHC Inc. is thus suppressed;
  the different steps of the procedure are simple, and do not take much time. They can easily be realized sequentially one after the other, without interruption, like for the classical stereotactic procedure with a frame;
  the patient does not have to carry the anchors for several days, thereby minimizing the risk of persistent pain and infection.

Moreover, the procedure can easily be changed and adapted during the operation, by several ways. The surgeon can for instance use the x-y table on the tripod to translate slightly the trajectory during the operation, or simply do another calibration in real time.

The use of a calibration device 8 ensures optimal precision, by placing the precision constraints on the positioning of the calibration target 11, where high precision can be achieved, and not in the orientation of the central joint of the tripod, where important errors reported at the tip of the tool (needle, electrode) can be induced by small errors in the orientation of the joint.

For the surgeon, the procedure requires minimal training. It is actually simpler than known techniques because of the smaller size and weight of the devices.

For the patient, the procedure using the invention is more precise, safer and really more comfortable than the classical procedure with frame and than the one using the STarFix device mentioned above, which involved several days of waiting with anchors implanted on the head until the personalized tripod was available.

Finally, the foreseen cost of the systems, including hardware and software, is substantially lower than the cost of a neurosurgical robot, making it affordable to any neurosurgical service.

The invention is not limited to the system and method discussed above and modifications are possible, for example by using equivalent means.

Also, the illustrative example given concerns a neurosurgical intervention, but of course other surgical and non-surgical applications are possible with the disclosed devices and methods of the invention and this description should not be construed as limiting in this respect.

REFERENCE NUMBERS 1 skull of a patient
2 anchor
2' anchor
2" anchor
2" calibre
3 screw (for the anchors)
4 screw (for the anchors)
4' screw (for the anchors)
4" screw (for the anchors)
5 marker
5' marker
5" marker
6 insertion guide device (IGD)
7 insertion guide
8 calibration device
9 calibration anchor
9' calibration anchor
9" calibration anchor
10 calibration marker
10' calibration marker
10" calibration marker
11 calibration target point
12 real target
13 surgical calibration device
14 surgical device
15 hole in skull

The invention claimed is:

1. System for stereotaxy of several different patients, comprising
 at least three anchors intended to be attached to a patient being treated and equipped with markers, wherein each of said markers is directly attached to a top portion of each of said anchors, which thereby results in an anchors and markers combination, wherein each anchors and markers combination is individually positionable on the patient;
 an insertion guide device with an insertion guide removably attached to the anchors and markers combination,
 an external calibration device with at least three calibration markers corresponding to said markers attached to the patient, wherein the at least three calibration markers are directly attached to at least a portion of the external calibration device, and
 a planning and imaging software;
 wherein the insertion guide is removably attached directly to said markers of the calibration device; and
 wherein the calibration device is adaptable to the patient being treated for orienting the insertion guide to reach the target point in the patient by orienting said guide on the calibration device reproducing a calibration target corresponding to the patient target point, wherein once the position of said target point in the patient with respect to the markers attached to the patient has been determined by said planning and imaging software, the insertion guide of the insertion guide device mounted on said calibration markers is calibrated and oriented using the determination of said software before the insertion guide device is mounted on said markers attached to the patient such that the insertion guide is thereby oriented towards the target point in the patient.

2. A system as defined in claim 1, wherein said system comprises three anchors with three markers.

3. A system as defined in claim 1, wherein said system comprises a calibre for placing the anchors such that the markers are in a predetermined position corresponding to the position of the calibration markers.

4. A system as defined in claim 1, wherein the markers are removably attached to the anchors.

5. A system as defined in claim 1, wherein said system comprises imaging markers used only for imaging purposes in imaging steps and replacement markers used for other steps of a method comprising at least the following steps:
 placing and attaching at least three anchors with markers on a patient;
 determining a target point and its position relatively to the markers;
 providing a calibration device having at least three calibration markers having the same relative position as the markers on the patient;
 placing a calibration target point having the same position relatively to the calibration markers than the target point with respect to the markers on the patient;
 placing an insertion guide device with an insertion guide on said calibration markers;
 inserting a surgical calibration device in said insertion guide and orienting said insertion guide so that the surgical calibration device reaches the calibration target point;
 blocking the position of the insertion guide in the insertion guide device;
 transferring the insertion guide device from the calibration markers onto the markers on the patient in order to be able to carry out a surgical intervention.

6. A method for using the system as defined in claim 1 comprising at least the following steps:
 placing and attaching at least three anchors with markers on a patient;
 determining a target point and its position relatively to the markers;
 providing a calibration device having at least three calibration markers having the same relative position as the markers on the patient;

placing a calibration target point having the same position relatively to the calibration markers than the target point with respect to the markers on the patient;

placing an insertion guide device with an insertion guide on said calibration markers;

inserting a surgical calibration device in said insertion guide and orienting said insertion guide so that the surgical calibration device reaches the calibration target point;

blocking the position of the insertion guide in the insertion guide device;

transferring the insertion guide device from the calibration markers onto the markers on the patient in order to be able to carry out a surgical intervention.

7. A method as defined in claim 6, wherein the position of the target point relatively to the markers is determined in an 3D imaging process.

8. A method as defined in claim 6, wherein the relative position of the calibration markers is transferred to the markers fixed to the patient.

9. A method as defined in claim 6, wherein the relative position of the markers fixed to the patient is transferred to the calibration markers.

10. A method as defined in claim 6, wherein the markers fixed to the patient comprise two sets of markers; a first set of markers used for the determination of the position of the target relatively to the markers, and a second set of markers used to support the insertion guide device during the surgical intervention.

11. A method as defined in claim 10, wherein the first set of markers is made of a material compatible with an imaging system and visible on the images produced by the imaging system.

* * * * *